United States Patent
Katsumoto et al.

(10) Patent No.: US 10,222,314 B2
(45) Date of Patent: Mar. 5, 2019

(54) FLOW CHANNEL DEVICE, COMPLEX PERMITTIVITY MEASURING APPARATUS, AND DIELECTRIC CYTOMETRY SYSTEM

(75) Inventors: Yoichi Katsumoto, Tokyo (JP); Shinji Omori, Tokyo (JP)

(73) Assignee: Sony Corporation, Tokyo (JP)

( * ) Notice: Subject to any disclaimer, the term of this patent is extended or adjusted under 35 U.S.C. 154(b) by 197 days.

(21) Appl. No.: 13/142,701

(22) PCT Filed: Jan. 7, 2010

(86) PCT No.: PCT/JP2010/050366
§ 371 (c)(1), (2), (4) Date: Jun. 29, 2011

(87) PCT Pub. No.: WO2010/079844
PCT Pub. Date: Jul. 15, 2010

(65) Prior Publication Data
US 2011/0269221 A1    Nov. 3, 2011

(30) Foreign Application Priority Data

Jan. 9, 2009    (JP) .................................. 2009-003648
Dec. 21, 2009    (JP) .................................. 2009-289465

(51) Int. Cl.
*G01N 15/12*    (2006.01)
*G01N 15/10*    (2006.01)
*C40B 60/14*    (2006.01)

(52) U.S. Cl.
CPC ......... *G01N 15/12* (2013.01); *G01N 15/1031* (2013.01); *G01N 15/1056* (2013.01);
(Continued)

(58) Field of Classification Search
CPC ...... B82Y 10/00; B82Y 40/00; H01J 37/3174; G01N 15/1031; G01N 15/1056;
(Continued)

(56) References Cited

U.S. PATENT DOCUMENTS 3,836,849 A    9/1974    Coulter et al.
4,298,836 A    11/1981    Groves et al.
(Continued)

FOREIGN PATENT DOCUMENTS

JP    HEI 07-239316    9/1995
JP    HEI 11-127846    5/1999
(Continued)

OTHER PUBLICATIONS

Morgan et al., "Single cell dielectric spectroscopy", J. Phys. D. Appl. Phys., 2007, pp. 61-70, vol. 40.
(Continued)

*Primary Examiner* — Dean Kwak
(74) *Attorney, Agent, or Firm* — K&L Gates LLP

(57) ABSTRACT

A flow channel device, a complex permittivity measuring apparatus, and a dielectric cytometry system are provided which can improve the measurement accuracy. A constriction portion having a constricted space is disposed between an inflow port and an outflow port of a flow channel. Electrodes are arranged between the inflow port and the constriction portion and between the outflow port and the constriction portion. The conductance of the constriction portion at a low-limit frequency is less than the combined conductance of an inflow channel portion and an outflow channel portion. The capacitance of the constriction portion at a high-limit frequency is less than the combined capacitance of the inflow channel portion and the outflow channel portion.

21 Claims, 12 Drawing Sheets

(52) U.S. Cl.
CPC ............... *G01N 2015/1006* (2013.01); *G01N 2015/1254* (2013.01)

(58) Field of Classification Search
CPC ........... G01N 15/12; G01N 2015/1254; G01N 27/026; G01N 33/4905; G01N 33/86
USPC ............................ 422/73, 501–505; 436/180
See application file for complete search history.

(56) References Cited

U.S. PATENT DOCUMENTS

| | | | |
|---|---|---|---|
| 5,665,979 A * | 9/1997 | Takahashi | B82Y 10/00 257/14 |
| 5,686,309 A | 11/1997 | Frank et al. | |
| 6,444,173 B1 * | 9/2002 | Sjursen | B01L 3/0268 204/600 |
| 6,537,799 B2 * | 3/2003 | Chow et al. | 435/285.2 |
| 7,520,164 B1 * | 4/2009 | Ayliffe | G01N 15/1056 324/71.1 |
| 8,128,795 B2 * | 3/2012 | Egawa | G01N 27/3272 204/403.01 |
| 8,246,805 B2 * | 8/2012 | Shinoda | 204/601 |
| 8,383,061 B2 * | 2/2013 | Prakash | F16K 99/0001 422/502 |
| 8,828,320 B2 * | 9/2014 | Bardell et al. | 422/68.1 |
| 2005/0118705 A1 * | 6/2005 | Rabbitt | B01L 3/502761 435/287.1 |
| 2006/0199173 A1 | 9/2006 | Thielecke et al. | |
| 2008/0164155 A1 * | 7/2008 | Pease | B01L 3/5027 205/777.5 |
| 2009/0201035 A1 | 8/2009 | Kaltenbach et al. | |
| 2010/0136606 A1 | 6/2010 | Katsumoto et al. | |

FOREIGN PATENT DOCUMENTS

| | | |
|---|---|---|
| JP | 2004-257766 | 9/2004 |
| JP | 2005-091098 | 4/2005 |
| JP | 2007-170850 | 7/2007 |
| JP | 2007-526462 | 9/2007 |
| JP | 2008-215901 | 9/2008 |
| JP | 2008-249681 | 10/2008 |
| JP | 2011-112497 A | 6/2011 |
| WO | 2009/022536 AW | 2/2009 |

OTHER PUBLICATIONS

Japanese Patent Office, Office Action issued in connection with Japanese Patent Application No. 2009-289465, dated Jan. 28, 2014. (3 pages).

Extended European Search Report dated Jan. 24, 2017 in corresponding European application No. 10729262.5 (12 pages).

Asami, Koji, Characterization of heterogeneous systems by dielectric spectroscopy, Progress in Polymer Science, 27 (2002), pp. 1617-1659.

Hoffman et al., Flow Cytometric Electronic Direct Current Volume and Radiofrequency Impedance Measurements of Single Cells and Particles, Society for Analytical Cytology, vol. 1, No. 6, 1981, pp. 377-384.

* cited by examiner

[FIG.1]
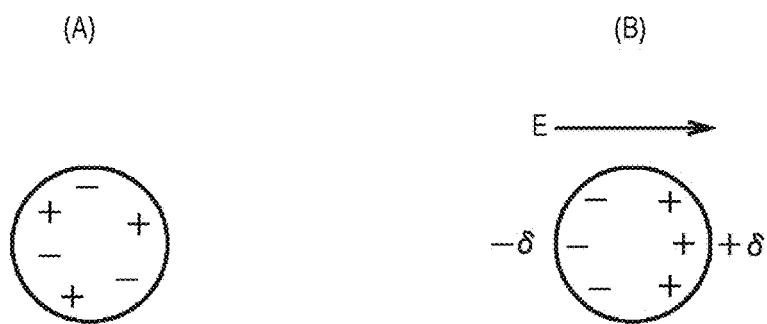
[FIG.2]
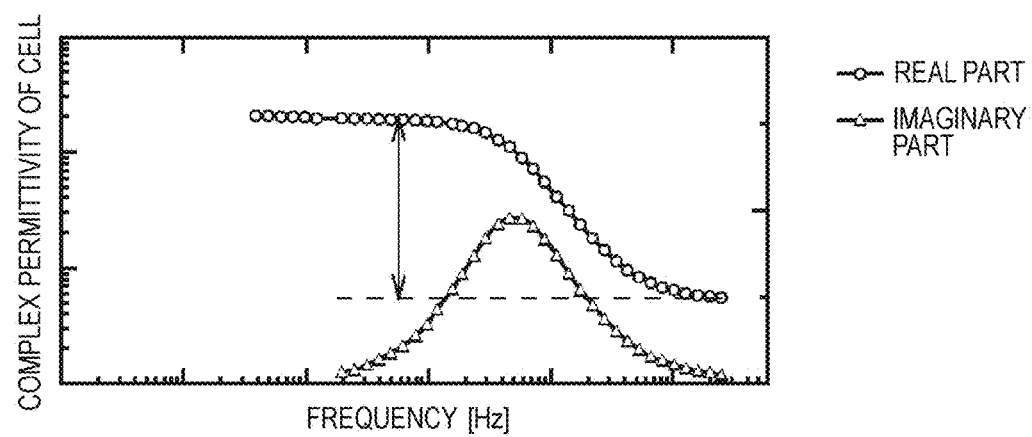

[FIG.3]
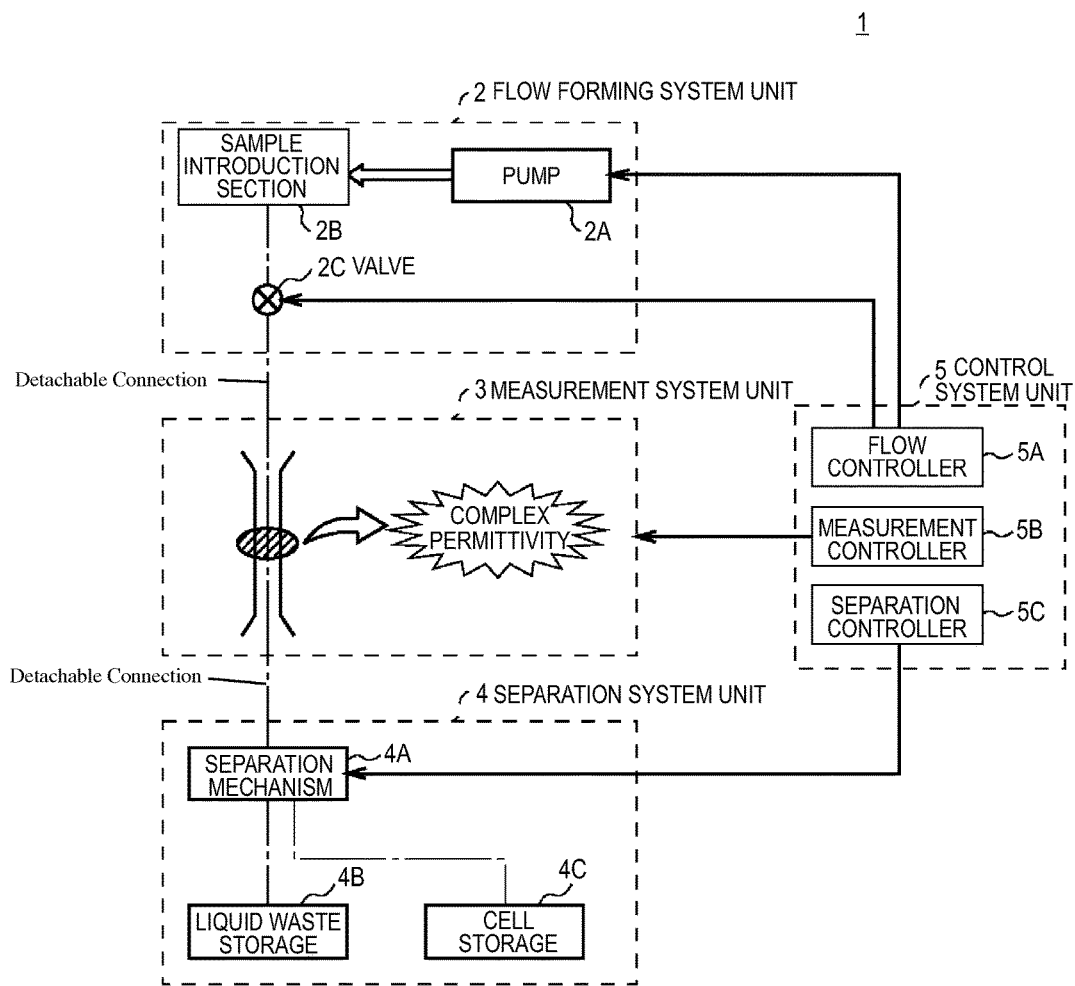

[FIG.4]
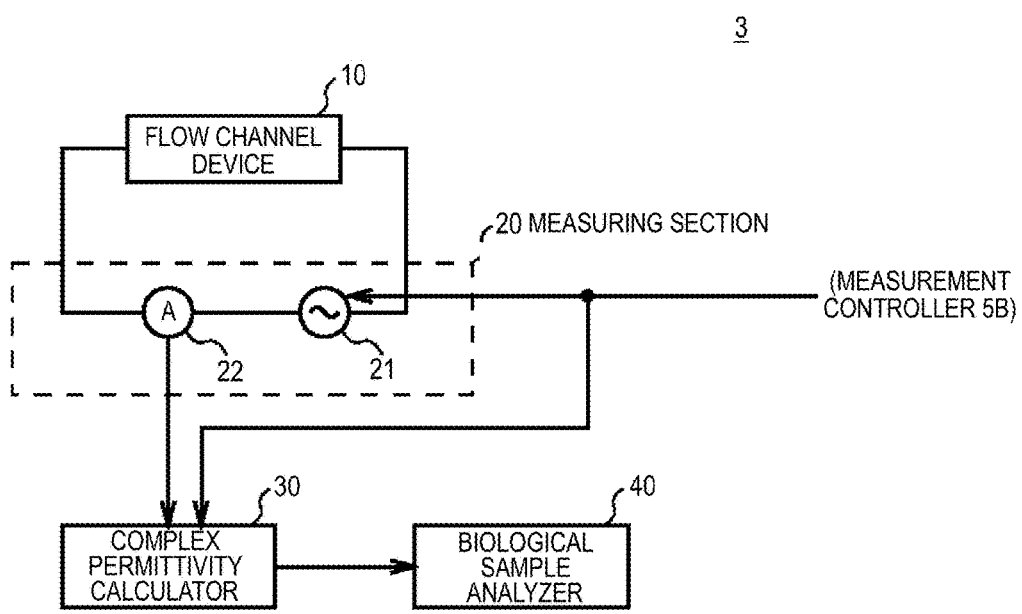

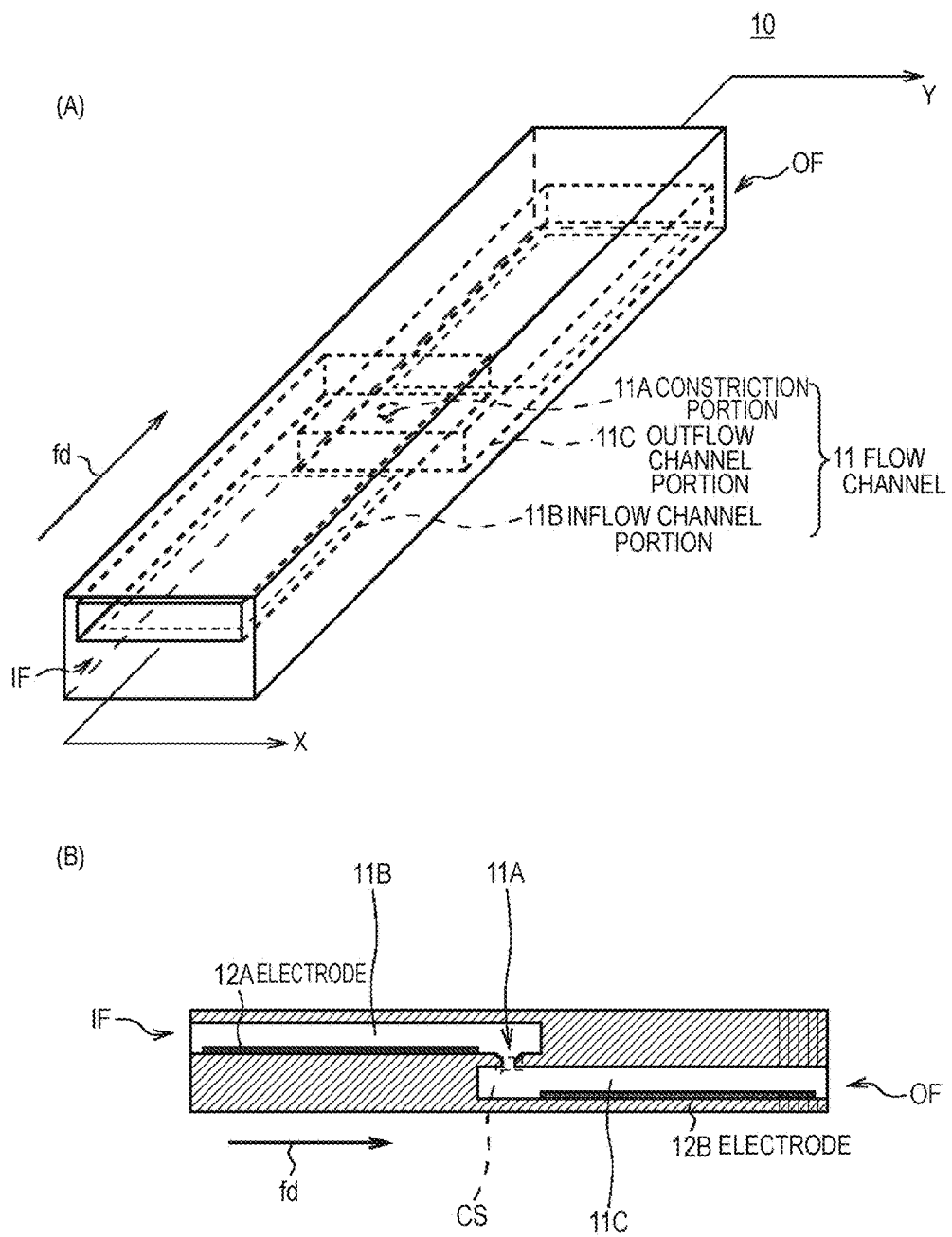
[FIG.5]

[FIG.6]
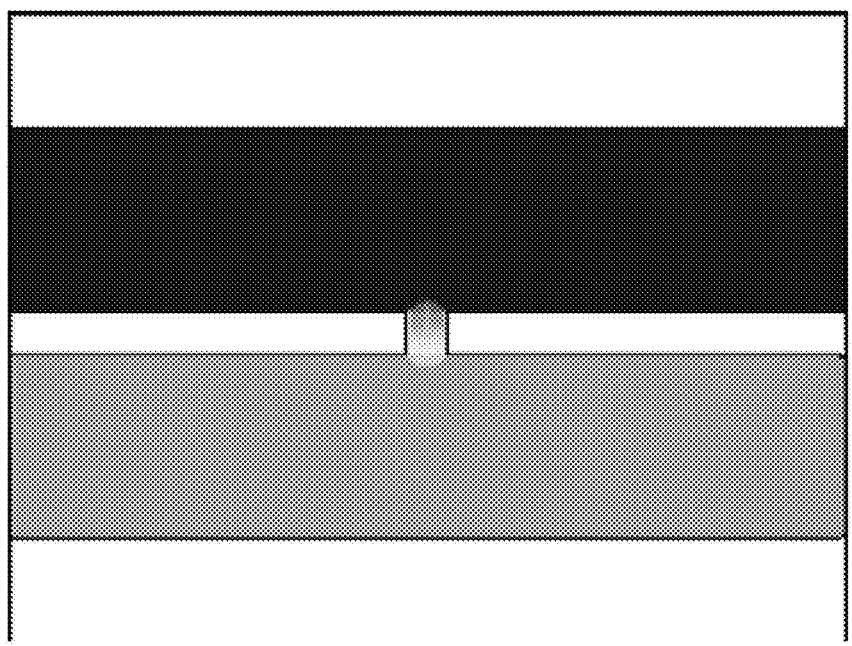

[FIG.7]
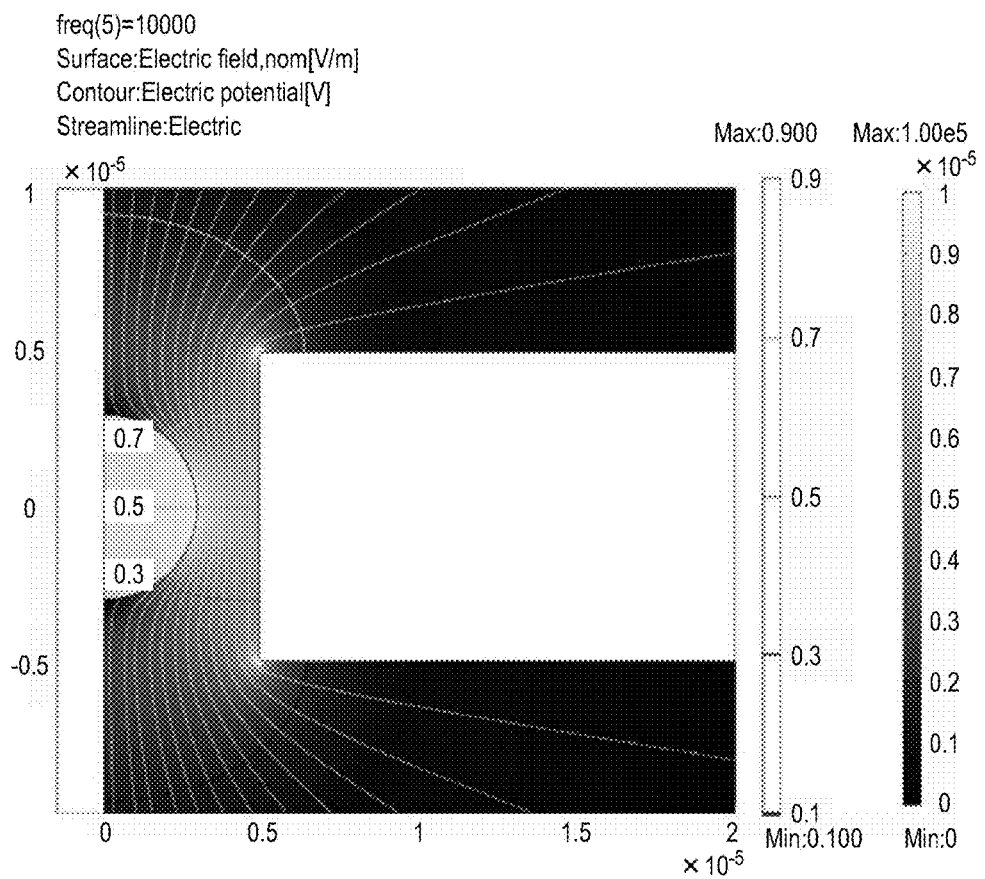

[FIG.8]
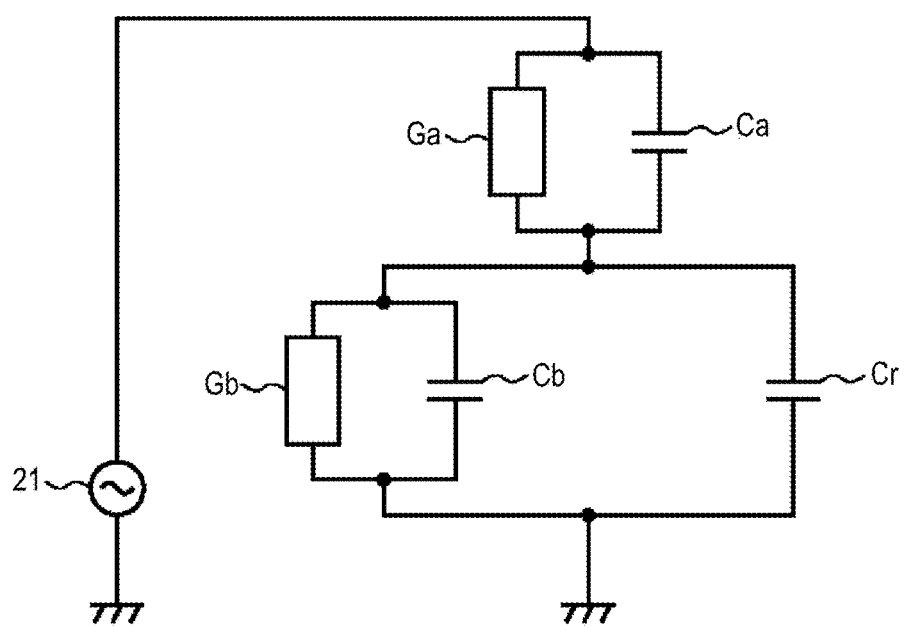

[FIG.9]
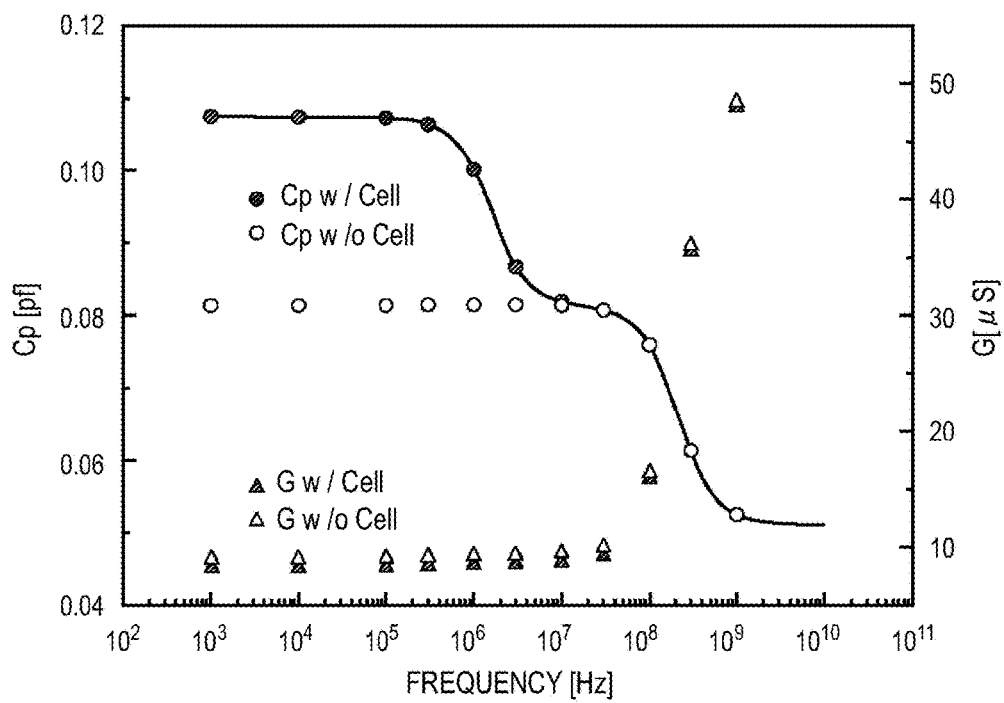

[FIG.10]
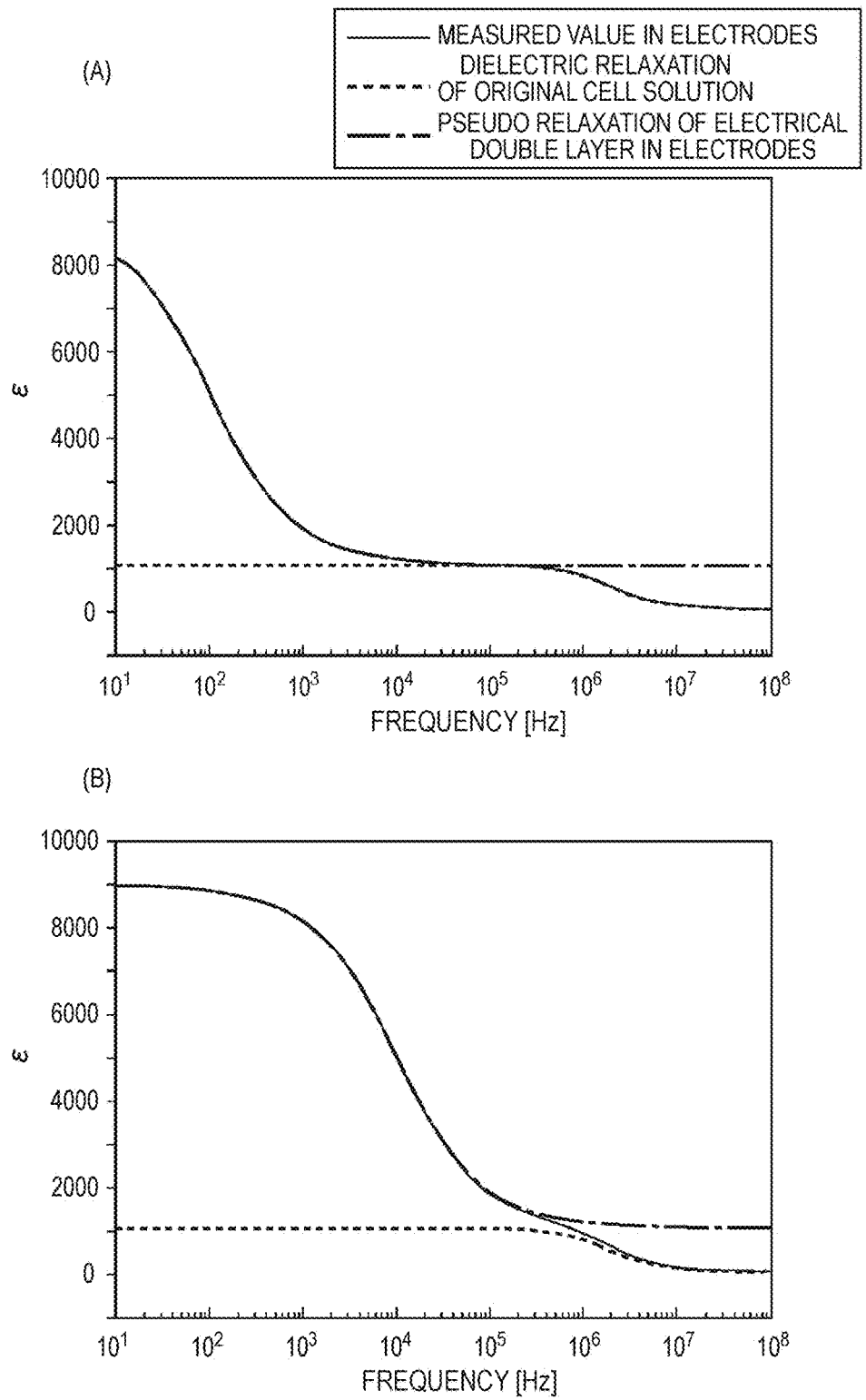

[FIG.11]
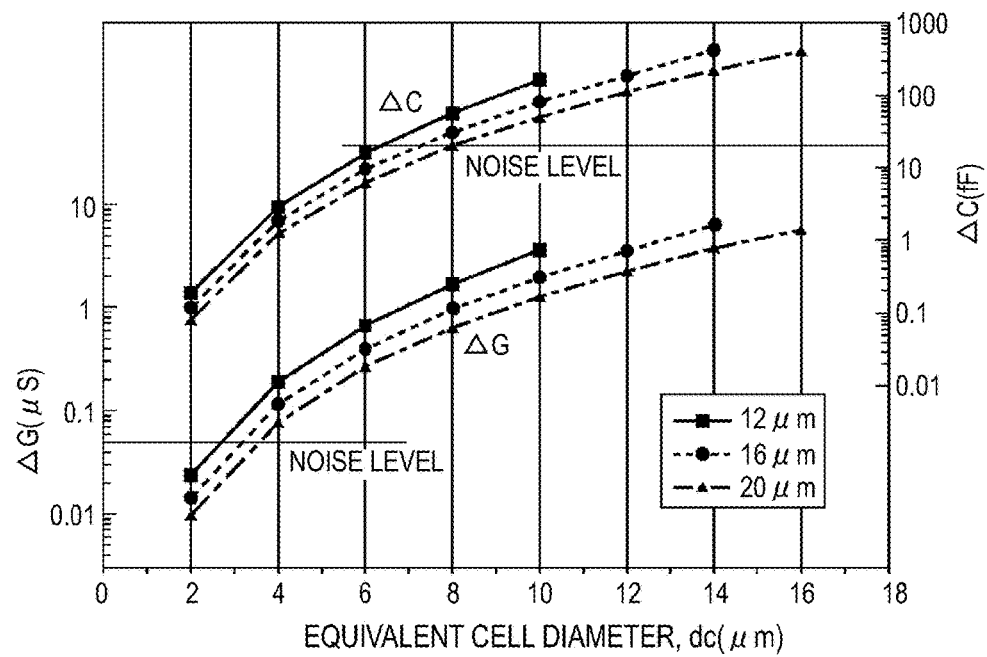

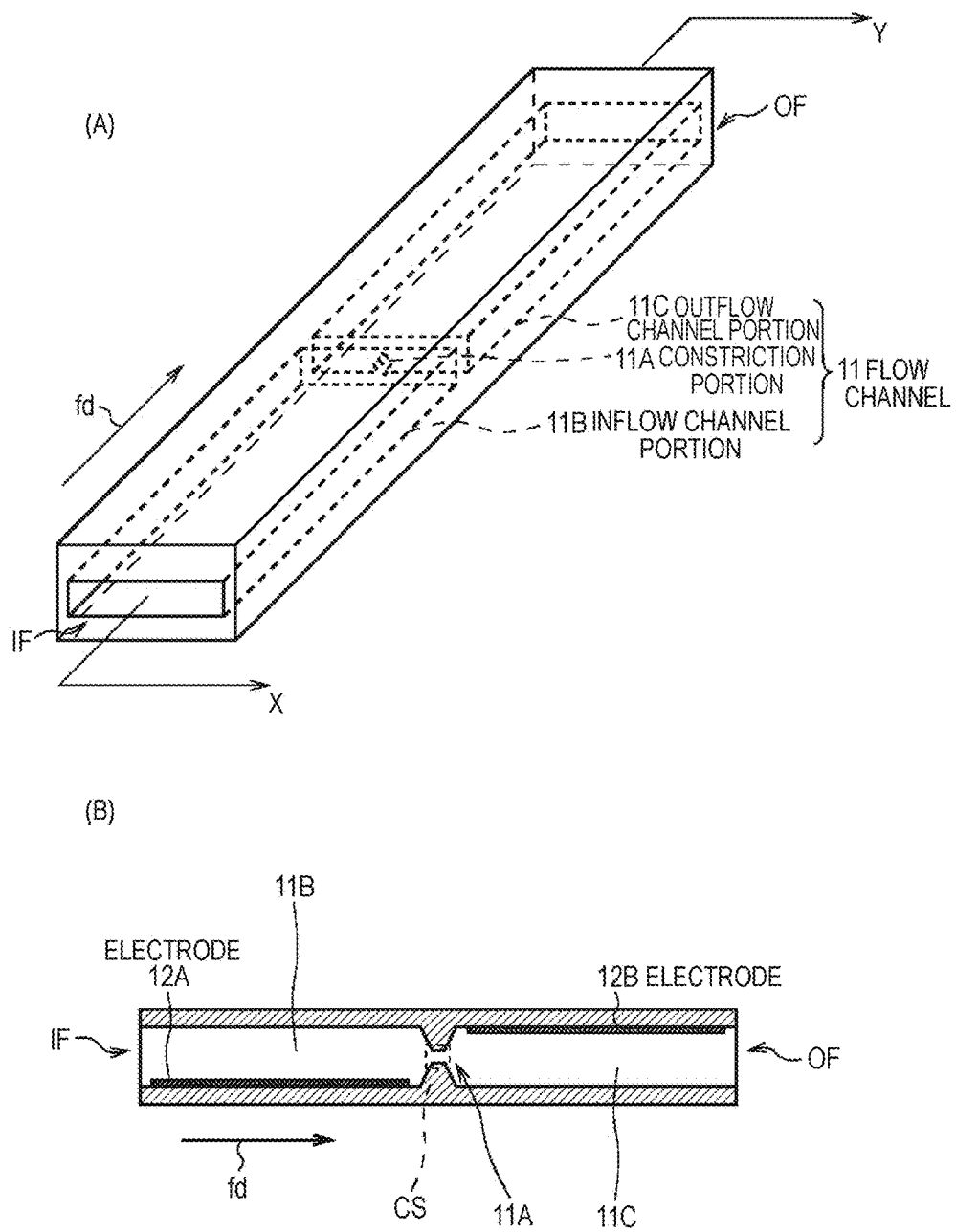
[FIG.12]

[FIG.13]
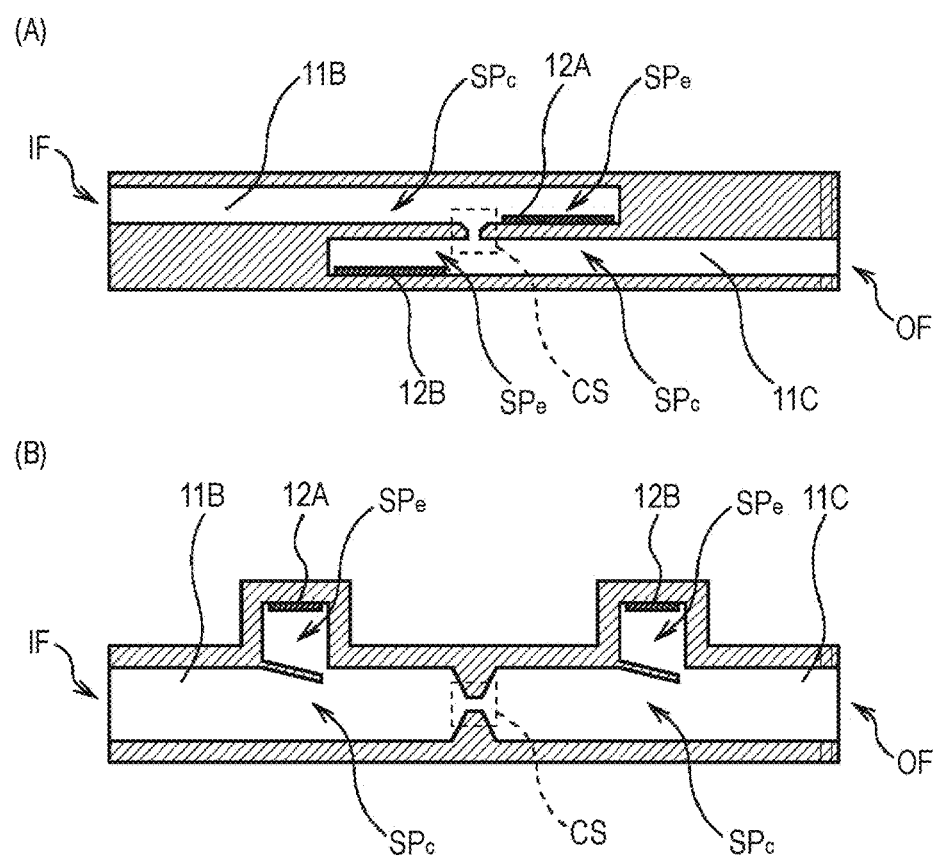

FLOW CHANNEL DEVICE, COMPLEX PERMITTIVITY MEASURING APPARATUS, AND DIELECTRIC CYTOMETRY SYSTEM

CROSS REFERENCE TO RELATED APPLICATIONS

The present application is a National Stage of International Application No. PCT/JP2010/050366 filed on Jan. 7, 2010, which claims priority to Japanese Patent Application No. 2009-003648, filed in the Japanese Patent Office on Jan. 9, 2009 and Japanese Patent Application No, 2009-289465, filed in the Japanese Patent Office on Dec. 21, 2009, the entire contents of which are being incorporated herein by reference.

BACKGROUND

The present invention relates to a technique of measuring the frequency dispersion (dielectric spectrum) of complex relative permittivity (hereinafter, abbreviated as complex permittivity) from a liquid containing biological samples such as cells and calculating physical properties of the biological samples or determining the cell type thereof from the measurement result.

A method of measuring an average dielectric spectrum of a liquid which contains plural cells has been known as a technique of measuring a dielectric spectrum of a cell. In this measuring method, unlike the case where the dielectric spectrums of individual cells are measured, an application of distinguishing one abnormal cell from 100 cells on the basis of the measured physical property information of cells is intrinsically impossible.

The complex permittivity or the frequency dispersion thereof is generally calculated by electrically measuring the complex capacitance or the complex impedance between electrodes using a solution retainer having electrodes used to apply an electric field to a solution.

Regarding the technique of measuring dielectric spectrums of individual cells contained in a liquid, an apparatus including a flow channel allowing the individual cells to sequentially flow and two plate electrodes, which are disposed parallel and opposite to each other on a part of the internal surface of the flow channel, with the same size as the cells has been proposed (for example, see NPL 1).

CITATION LIST

[NPL 1] Hywel Morgan Tao Sun, David Holmes, Shady Gawad, and Nicolas G Green (Nanoscale Systems Integration Group, School of Electronics and Computer Science, University of Southampton, SO17 1BJ UK), Single cell dielectric spectroscopy, JOURNAL OF PHYSICS D: APPLIED PHYSICS, Appl. Phys. 40 (2007) 61-70

SUMMARY

When an electric field is applied to a solution containing cells by the use of electrodes, a phenomenon called electrode polarization irreversibly occurs and thus the complex capacitance of the solution containing cells to be measured is coupled in series to the capacitance of an electrical double layer formed in the interface between the electrodes and the solution. In general, the capacitance of the electrical double layer is very large and shows relaxation (hereinafter, also referred to as "electrode polarization relaxation").

When the characteristic frequency indicating the electrode polarization relaxation is $f_{EP}$, the capacitance of the electrical double layer is $C_s$, and the conductivity of the overall flow channel is $G_t$, the characteristic frequency $f_{EP}$ can be expressed by the following expression.

$$f_{EP} = \frac{1}{2\pi} \cdot \frac{G_t}{C_s} \quad (1)$$

Here, the capacitance $C_s$ of the electrical double layer is proportional to the surface area of the electrode. Accordingly, as the area of the electrode increases, the characteristic frequency $f_{EP}$ indicating the electrode polarization relaxation is lowered.

However, when two plate electrodes with the same size as a cell are disposed parallel and opposite to each other, the characteristic frequency $f_{EP}$ acquired from Expression 1 reaches the order of MHz which is a frequency band in which dielectric relaxations of the cells to be measured exist.

Therefore, in NPL 1, there is a problem in that the frequency dispersion of the electrode polarization relaxation is mixed into the frequency dispersion of the complex permittivity of a solution containing the individual cells, whereby the dielectric spectrums of the cells cannot be measured accurately.

The invention is made in consideration of the above-mentioned problems and a goal thereof is to provide a flow channel device, a complex permittivity measuring apparatus, and a dielectric cytometry system which can improve the measurement accuracy for dielectric spectrums of individual cells.

To accomplish this goal, according to the invention, there is provided a flow channel device having formed therein a flow channel through which a liquid containing a plurality of biological samples from which complex permittivity should be measured flows, including: a constriction portion that is disposed between an inflow port and an outflow port of the flow channel and that includes an inlet and an outlet through which a single biological sample of the plurality of biological samples can pass; an electrode that is disposed in a flow channel portion between the inflow port of the flow channel and the inlet of the constriction portion and that serves as one application target of an alternating voltage; and an electrode that is disposed in a flow channel portion between the outlet of the constriction portion and the outflow port of the flow channel and that serves as the other application target of the alternating voltage.

In the flow channel device, the conductance of the constriction portion at a low-limit frequency is smaller than the conductance of the flow channel portions and the capacitance of the constriction portion at a high-limit frequency is smaller than the capacitance of the flow channel portion.

Accordingly, in the flow channel device according to the invention, when the alternating voltage is applied to the electrodes, the voltage drop of the constriction portion is relatively large, compared with the voltage drop in the flow channel portion from the inflow port to the inlet of the constriction portion and in the flow channel portion from the outlet of the constriction portion to the outflow port, and an electric field is thus concentrated on the constriction portion.

That is, the flow channel device according to the invention can be set to the same state as a case where electrodes having an area equivalent to that of the ports are disposed in the portions of the constriction portion close to the inflow port and the outflow port. As a result, even when electrodes much larger than the size equivalent to that of the biological sample are used in the flow channel device, it is possible to obtain the sensitivity sufficient to measure the complex permittivity from a single biological sample or an extremely small number of biological samples.

Therefore, it is possible to implement a flow channel device, a complex permittivity measuring apparatus, and a dielectric cytometry system which can improve the measurement accuracy for dielectric spectrums of individual cells.

Additional features and advantages of the present invention are described herein, and will be apparent from, the following Detailed Description and the Figures.

BRIEF DESCRIPTION THE FIGURES

FIG. 1 is a diagram schematically illustrating the relation between ions in a cell and an electric field.

FIG. 2 is a graph illustrating the dielectric spectrum of a cell.

FIG. 3 is a diagram schematically illustrating the configuration of a dielectric cytometry system.

FIG. 4 is a block diagram illustrating the configuration of a measurement system unit.

FIG. 5 is a diagram schematically illustrating the configuration of a flow channel device.

FIG. 6 is a diagram schematically illustrating the simulation result of a potential distribution.

FIG. 7 is a diagram schematically illustrating the simulation result of a current flux.

FIG. 8 is a circuit diagram illustrating an equivalent circuit in the flow channel device.

FIG. 9 is a graph illustrating a dielectric spectrum obtained by numerical analysis.

FIG. 10 is a graph illustrating the relation among the dielectric relaxation of a cell solution, the pseudo relaxation of an electrical double layer in electrodes, and measured values, where FIG. 10(A) shows an example with a surface area where the characteristic frequency representing the electrode polarization relaxation is 100 [Hz] and FIG. 10(B) shows an example with a surface area where the characteristic frequency is 10 [Hz].

FIG. 11 is a graph illustrating a variation in capacitance and a variation in conductance in a constricted space with respect to a cell diameter.

FIG. 12 is a diagram schematically illustrating the configuration of a flow channel device according to another embodiment of the invention.

FIG. 13 is a diagram schematically illustrating the configuration of a flow channel device according to still another embodiment of the invention.

DETAILED DESCRIPTION

Hereinafter, embodiments of the invention will be described. The description will be made in the following order of contents.

<1. Electrical Characteristics of Cell>
[1-1. Relation between Complex Permittivity of Cell and Frequency of Alternating Electric Field]
[1-2. Parameters of Dielectric Spectrum and Applications thereof]
[1-3. Method of Calculating Complex Permittivity]
<2. Embodiment>
[2-1. Configuration of Dielectric Cytometry System]
[2-2. Configuration of Measurement System Unit]
[2-3. Conditions of Flow Channel Device]
[2-4. Advantages]
<3. Other Embodiments>

1. Electrical Characteristics of Cell

Electrical characteristics of cells will be described in terms of the relation between the complex permittivity of a cell and the frequency of an alternating electric field, parameters (hereinafter, referred to as dielectric parameters) of a dielectric spectrum and applications thereof, and a method of calculating the complex permittivity.

[1-1. Relation Between Complex Permittivity of Cell and Frequency of Alternating Electric Field]

The cytoplasm includes cations and anions (FIG. 1(A)). The ions move with (follow) a change in the positive and negative directions of the alternating electric field when a cell exists in the alternating electric field. In this case, since a cell membrane has a highly insulating property, the ions in the cytoplasm gather in the vicinity of the cell membrane and the cations and the anions are eccentrically located in the interface between the cell membrane and the cytoplasm to cause polarization (FIG. 1(B)).

Here, a simulated dielectric spectrum is shown in FIG. 2. As can be seen from FIG. 2, when the frequency of the alternating electric field is sufficiently low, the cell is polarized at the interface and thus the real part of the complex permittivity is obtained as a great value.

On the other hand, when the frequency of the alternating electric field becomes approximately several tens of MHz, the direction of the alternating electric field is reversed before the cations and the anions move to the interface between the cell membrane and the cytoplasm. That is, the interface polarization cannot follow the change of the alternating electric field.

Therefore, as the frequency of the alternating electric field becomes higher, the real part of the complex permittivity becomes smaller. In this way, the phenomenon that the complex permittivity varies depending on the frequency is referred to as "dielectric relaxation".

The dielectric relaxation occurs with a specific frequency band as a boundary depending on the size or structure of a cell. The number of dielectric relaxations depends on the number and shape of significant interfaces included in the cell. For example, in cells such as red corpuscles having no cell nucleus, the number of dielectric relaxations is 1. In nucleate cells having one or two or more nuclei, the number of dielectric relaxations is two or more.

In this way, the complex permittivity of a cell depends on the frequency of an electric field. This is referred to as "dielectric dispersion".

[1-2. Parameters of Dielectric Spectrum and Applications Thereof]

The dielectric spectrum of a cell shown in FIG. 2 can be expressed by the following expression.

$$\varepsilon*(\omega) = \sum_{m=1}^{n} \frac{\Delta\varepsilon_m}{(1+(j\omega\tau_m)^{\alpha_m})^{\beta_m}} + \varepsilon_h + \frac{k_1}{j\omega\varepsilon_v}. \quad (2)$$

In Expression 2, "$\varepsilon*$" represents the complex permittivity, "$\omega$" represents the angular frequency, "j" represents the imaginary number unit, "$\varepsilon_h$" represents the high-limit frequency value of the relative permittivity, "$\kappa_1$" represents the low-limit frequency value of the conductivity, "$\varepsilon_v$" represents the vacuum permittivity, and "n" represents the number of dielectric relaxations.

"$\Delta\varepsilon_m$" represents the relaxation strength of the m-th dielectric relaxation (the difference between the maximum and the minimum of the relative permittivity in the m-th dielectric relaxation portion) and "$\tau_m$" represents the relaxation time of the m-th dielectric relaxation (the value obtained by dividing a reciprocal of an intermediate frequency of the frequency range corresponding to the m-th dielectric relaxation by $2\pi$). "$\alpha_m$" represents the variable indicating the shape of the dielectric spectrum distribution and "$\beta_m$" represents the variable indicating the shape of the dielectric spectrum distribution from the viewpoint different from "$\alpha_m$".

"$\Delta\varepsilon_m$", "$\tau_m$", "$\alpha_m$", and "$\beta_m$" are dielectric parameters characterizing the shape of the dielectric spectrum and depend on the type, shape, structure, or composition of a cell. Accordingly, when the dielectric parameters are obtained, cells can be separated depending on the types, or heterogeneous cells can be detected and separated from the homogeneous cells, or the composition or state of a cell can be analyzed. In addition, dielectric parameters other than "$\Delta\varepsilon_m$", "$\tau_m$", "$\alpha_m$", and "$\beta_m$" can be determined but are not described herein.

[1-3. Method of Calculating Complex Permittivity]

The current and the voltage satisfy the following expression.

$$I^*(\omega) = (G + j\omega C) V^*(\omega) \tag{3}$$

In Expression 3, "I" represents the current, "V" represents the voltage, "G" represents the conductance of a solution containing cells, "C" represents the capacitance of the solution containing cells, and "*" represents a complex number.

On the other hand, the conductance, the capacitance, and the complex permittivity satisfy the following expression.

$$G + j\omega C = j\omega \varepsilon^*(\omega) C_1 \tag{4}$$

In Expression 4, "$C_1$" represents a constant depending on the structure of a flow channel device.

The frequency at which normal red corpuscles or white corpuscles indicate a dielectric relaxation is about 2 MHz and the frequency band in which the whole cells of corpuscles (blood cells) show the dielectric relaxation is substantially from 100 kHz to 10 MHz.

Accordingly, when a cell to be measured is a blood cell, an alternating voltage is applied between electrodes while changing the frequency in the broad frequency band of several hundreds of kHz to several tens of MHz and the current is measured. Then, the complex permittivity of the solution containing the blood cell can be calculated for each frequency on the basis of Expressions 3 and 4, thereby obtaining the dielectric spectrum of the blood cell. By applying the obtained dielectric spectrum to Expression 2, it is possible to calculate the dielectric parameters.

As the stride of the frequency of the alternating voltage is narrowed, the frequency dependency of the dielectric parameters can be obtained more accurately. The narrowed stride of the frequency and the time necessary for measuring the individual cells generally have a trade-off relation. Accordingly, it is important to comprehensively improve the measurement accuracy.

2. Embodiments

A dielectric cytometry system according to an embodiment of the invention will be described below.

[2-1. Configuration of Dielectric Cytometry System]

FIG. 3 shows the schematic configuration of a dielectric cytometry system 1. The dielectric cytometry system 1 includes a flow forming system unit 2, a measurement system unit 3, a separation system unit 4, and a control system unit 5.

The flow forming system unit 2 gives a pressure by the use of a pump 2A to send a solution containing a cell to be measured from a sample introduction section 2B to a valve 2C and to emit the solution through the valve 2C.

The measurement system unit 3 includes a flow channel communicating with the valve 2C and an alternating voltage is applied to a pair of electrodes disposed in the flow channel. The measurement system unit 3 measures the current flowing in the electrodes, calculates the complex permittivity of the solution containing cells from the measurement result, and derives a dielectric spectrum or dielectric parameters therefrom.

In the separation system unit 4, a separation mechanism 4A separates the solution flowing out from the flow channel of the measurement system unit 3 into a liquid waste and a target cell-containing liquid, sends out the liquid waste to a liquid waste storage 4B, and sends out the target cell-containing liquid to a cell storage 4c.

The control system unit 5 includes a flow controller 5A, a measurement controller 5B, and a separation controller 5C. The flow controller 5A is supplied from an input interface (not shown) with setting information to be set for the pump 2A or the valve 2C in the flow forming system unit 2 or flow information regarding the flow of the solution.

The flow controller 5A sets a pressure initially set, or indicated by the setting information, or calculated on the basis of the flow information for the pump 2A, sets an aperture size for the valve 2C, and controls the flow rate and the flow quantity of the solution to be supplied to the measurement system unit 3.

The measurement controller 5B is supplied with the setting information to be set for the measurement system unit 3 from the input interface. The measurement controller 5B sets measurement information about the measurement such as the frequency stride or the frequency band initially set or indicated by the setting information for the measurement system unit 3 and controls the measuring conditions of the measurement system unit 3.

The separation controller 5C is supplied with setting information to be set for the separation mechanism 4A of the separation system unit 4 from the input interface. The separation controller 5C sets separation information initially set or indicated by the setting information for the separation mechanism 4A and controls the separating conditions of the separation system unit 4.

In the dielectric cytometry system 1, one of the flow forming system unit 2, the measurement system unit 3, and the separation system unit 4 is provided with a temperature sensor (not shown) and a thermoelectric device (not shown). The control system unit 5 can control the temperature of the solution by measuring the temperature of the solution by the use of the temperature sensor and supplying a signal corresponding to the measurement result to the thermoelectric device.

As the technique of measuring a cell flowing in the flow channel, a fluorescent flow cytometry is known in which a target sample marked by a fluorescent material is made to flow in the flow channel and a laser beam is applied to liquid droplets generated from the flow in a direction perpendicular to the flow. In this flow cytometry, an operation of adding a marker to the cell is necessary and it is often difficult to reuse the cell to which the marker has been added.

On the contrary, in this dielectric cytometry system 1, since the dielectric parameters or the physical properties of a cell are directly measured from the dielectric spectrum of the cell-containing solution flowing in the flow channel without marking with the fluorescent material, the disadvantages in the flow cytometry can be avoided. That is, it is very advantageous in that the fluorescent marking is not necessary and the physical properties of a cell can be known.

[2-2. Configuration of Measurement System Unit]

FIG. 4 schematically illustrates the configuration of the measurement system unit 3. The measurement system unit 3 includes a flow channel device 10, a measuring section 20, a complex permittivity calculator 30, and a biological sample analyzer 40.

The appearance of the flow channel device 10 is shown in FIG. 5(A) and a section taken along line X-Y of FIG. 5(A) is shown in FIG. 5(B). A hollow flow channel 11 is formed in the flow channel device 10.

In the flow channel 11, a constriction portion 11A is disposed between an inflow port IF and an outflow port OF. In this embodiment, the shape of a flow channel portion (hereinafter, also referred to as "an inflow channel portion") 11B between an inlet of the constriction portion 11A and the inflow port IF and the shape of a flow channel portion (hereinafter, also referred to as "an outflow channel portion") 11C between an outlet of the constriction portion 11A and the outflow port OF are substantially the same as each other.

In the flow channel 11 according to this embodiment, the inflow channel portion 11B and the outflow channel portion 11C are disposed in parallel in a state where their ends depart from each other in a direction perpendicular to a flow direction fd, and the constriction portion 11A is connected in the direction perpendicular to the flow direction fd between the end of the inflow channel portion 11B and the end of the outflow channel portion 11C.

The constriction portion 11A includes a cylindrical space (hereinafter, also referred to as "a constricted space") CS through which a single cell to be measured can pass. The constriction portion 11A according to this embodiment is provided with a taper inclined to the constricted space CS.

Therefore, when a solution is emitted to the inflow port IF from the valve 2C of the flow forming system unit 2, plural cells contained in the solution flow in the inflow channel portion 11B of the flow channel device 10 and are guided into the constricted space CS by the taper of the constriction portion 11A. The cells guided to the constricted space CS individually pass through the constricted space CS and flow through the outflow channel portion 11C to the outflow port OF.

Plate-like electrodes 12A and 12B are disposed on the side walls of the inflow channel portion 11B and the outflow channel portion 11C. An alternating voltage is applied to the electrodes 12A and 12B from an alternating voltage source 21 (FIG. 4) of the measuring section 20.

Here, in the flow channel device 10, the area of the electrodes 12A and 12B is sufficiently large than the opening of the constricted space CS. In the flow channel device 10 having the above-mentioned configuration, when the alternating voltage is applied to the electrodes 12A and 12B, the potentials of the inflow channel portion 11B and the outflow channel portion 11C provided with the electrodes 12A and 12B are kept substantially constant in their spaces, as shown in FIGS. 6 and 7. On the other hand, a relatively-large potential difference and electric field concentration are caused in the constricted space CS. Therefore, the complex permittivity of each cell passing through the constricted space CS is apparently reflected in the current between the electrodes 12A and 12B.

FIG. 6 shows a potential distribution in the flow channel by simulation in a section including the central axis of the constriction portion as viewed in the X-Y direction of FIG. 5(A). FIG. 7 shows a current flux at the time of passing a cell by simulation in the section including the central axis of the constriction portion as viewed in the X-Y direction of FIG. 5(A).

In the simulations in FIGS. 6 and 7, it is assumed that the height of the flow channel in the inflow channel portion 11B and the outflow channel portion 11C is 50 μm, the thickness (the length of the constriction portion in a direction in which a cell passes) of a layer constituting the constricted space CS is 12 μm, and the diameter (the length of the constriction portion in the direction perpendicular to the direction in which a cell passes) of the layer is 10 μm. It is assumed that the inflow channel portion 11B, the outflow channel portion 11C, and the constricted space CS are filled with a liquid with a relative permittivity of 78.3 and a conductivity of 1.67 S/m.

For reference, a classification of potential distributions of the electric field shown in FIG. 6 is appended. The cell properties in the simulation are referred to in the documents.

In the flow channel device 10, the inflow port IF and the outflow port OF are detachably coupled to an output end of the flow forming system unit 2 and an input end of the separation system unit 4 via a connection member such as a tube. The electrodes 12A and 12B are detachably connected to an output end of the alternating voltage source 21 (FIG. 4) via a signal line.

Accordingly, the flow channel device 10 can be attached to and detached from the dielectric cytometry system 1 (the measurement system unit 3). As a result, the flow channel device can be replaced depending on various situations such as the size of a cell to be measured or device cleaning.

The measuring section 20 (FIG. 4) includes an alternating voltage source 21 and an amperemeter 22. The alternating voltage source 21 is supplied with the measurement information from the measurement controller 5B of the control system unit 5. The alternating voltage source 21 generates an alternating voltage to be applied to the electrodes 12A and 12B on the basis of the details of the measurement information.

For example, the alternating voltage source 21 alternatively generates the alternating voltage at a high speed and at plural prescribed frequencies every setting time, which is a time when the overall cells to be measured exist in the constricted space CS and which is set on the basis of the information such as the size of a cell or the flow rate of a solution.

The amperemeter 22 measures a current flowing in the electrodes 12A and 12B (FIG. 5) and supplies data indicating the measurement result to the complex permittivity calculator 30. The data varies for each cell passing through the constricted space CS, as described above.

The complex permittivity calculator 30 calculates the complex permittivity at plural prescribed frequencies for each cell passing through the constricted space CS by the use of the data supplied from the amperemeter 22 and Expressions 1 and 2, and sends data indicating a dielectric spectrum as the calculation result to the biological sample analyzer 40.

The biological sample analyzer 40 calculates dielectric parameters by the use of the data supplied from the complex permittivity calculator 30 and generates data indicating the dielectric spectrum based on the dielectric parameters.

The biological sample analyzer 40 generates data for separating the cells by types or data for detecting and separating heterogeneous types from homogeneous type cells or data indicating the composition or state of the cells using the dielectric parameters as necessary.

In this way, the measurement system unit 3 measures the complex permittivity of a single cell passing through the constricted space CS along with a liquid medium.

[2-3. Conditions of Flow Channel Device]

The conditions of the flow channel device 10 of the measurement system unit 3 will be described below with reference to the equivalent circuit shown in FIG. 8. In FIG. 8, "$G_a$" represents the combined conductance of the inflow channel portion 11B and the outflow channel portion 11C and "$C_a$" represents the combined capacitance of the inflow channel portion 11B and the outflow channel portion 11C. "$G_b$" represents the conductance between the inlet and the outlet of the constriction portion 11A and "$C_b$" represents the capacitance between the inlet and the outlet of the constriction portion 11A. "$C_r$" represents the floating capacitance of a member (that is, a wall member forming the constricted space) around the constricted space CS.

When it is assumed that a cell exists in the constricted space CS (that is, which represents a debye type dielectric relaxation in the constricted space CS), the conductance "$G_b$" between the inlet and the outlet of the constriction portion 11A can be expressed by the following expression.

$$G_b = G_{bl} + \frac{(G_{bh} - G_{bl})\left(\frac{\omega}{\omega_0}\right)^2}{1 + \left(\frac{\omega}{\omega_0}\right)^2} \quad (5)$$

In this case, the capacitance "$C_b$" between the inlet and outlet of the constriction portion 11A can be expressed by the following expression.

$$C_b = C_r + C_{bh} + \frac{C_{bl} - C_{bh}}{1 + \left(\frac{\omega}{\omega_0}\right)^2} \quad (6)$$

In these expressions, "$\omega_0$" represents the relaxation angular frequency. "$G_{bl}$" represents the conductance between the inlet and the outlet of the constriction portion 11A at a low-limit frequency and "$G_{bh}$" represents the conductance between the inlet and the outlet of the constriction portion 11A at a high-limit frequency.

"$C_{bl}$" represents the capacitance between the inlet and the outlet of the constriction portion 11A at the low-limit frequency and "$C_{bh}$" represents the capacitance between the inlet and the outlet of the constriction portion 11A at the high-limit frequency.

As shown in FIG. 8, since the floating capacitance of a member $C_r$ around the constricted space CS is parallel to the constricted space CS, it can be simply added as expressed by Expression 6.

Here, the expression representing the total conductance and capacitance of the flow channel device 10 is complicated and thus is not described. On the other hand, the differences in conductance and capacitance between a case where the relaxation is not caused in the constriction portion 11A (where no cell exists in the constricted space CS) and a case where the relaxation is caused in the constriction portion 11A (where a cell exists in the constricted space CS) are simplified when $G_a > G_{bl}$ and $C_a > C_{bh}$ are satisfied.

That is, the difference in conductance $dG_h$ at the high-limit frequency can be expressed by the following expression.

$$dG_h = (G_{bh} - G_{bl}) \times \left(\frac{C_a}{C_a + C_{bh}}\right)^2 \sim G_{bh} - G_{bl} \quad (7)$$

The difference in capacitance $dC_l$ at the low-limit frequency can be expressed by the following expression.

$$dC_l = (C_{bl} - C_{bh}) \times \left(\frac{G_a}{G_a + G_{bl}}\right)^2 \sim C_{bl} - C_{bh} \quad (8)$$

The difference in capacitance $dC_h$ at the high-limit frequency and the difference in conductance $dG_l$ at the low-limit frequency are substantially zero.

As expressed by Expressions 7 and 8, when $G_a > G_{bl}$ and $C_a > C_{bh}$ are satisfied, the variations in capacitance and conductance in the entire flow channel device 10 are determined by the capacitance and the conductance of the constricted space CS of the constriction portion 11A.

In other words, the constricted space CS (with the sizes of the inlet and outlet and the volume from the inlet to the outlet which enable the single cell to pass) is determined depending on a cell to be measured. Accordingly, by designing the electrodes 12, the inflow channel portion 11B, and the outflow channel portion 11C so as to satisfy the above-mentioned conditions, it is possible to measure only the capacitance of the cell passing through the constriction portion 11A.

By suppressing the manufacturing deviation of the constriction portion 11A, it is possible to suppress the measuring deviation of the flow channel device 10 without strictly considering positions or an alignment error for arranging the electrodes 12A and 12B.

The calculation result of a dielectric spectrum obtained when a cell exists in the constricted space CS of the flow channel device 10 satisfying the above-mentioned conditions is shown in FIG. 9. An electrical double layer is not considered in numerical calculation. "Cp w/Cell" in FIG. 9 represents the capacitance dispersion when a cell exists in the constricted space CS and "Cp w/o Cell" represents the capacitance dispersion when no cell exists in the constricted space CS. "G w/Cell" represents the conductance dispersion when a cell exists in the constricted space CS and "G w/o Cell" represents the conductance dispersion when no cell exists in the constricted space CS.

As can be seen from FIG. 9, a dielectric relaxation (hereinafter, also referred to as "cell relaxation") due to a cell is caused on a low frequency side and a pseudo relaxation (hereinafter, also referred to as "structural pseudo relaxation") due to the structure in which layers having plural capacitances are connected in series as shown in FIG. 8 is caused on a high frequency side. The flow channel device can be designed so that the structural pseudo relaxation is caused on a higher frequency side than the frequency band at which the cell relaxation is caused, thereby not having an influence on the measurement result, as can be seen from FIG. 9.

On the other hand, although not shown in FIG. 9 because the simulation is impossible, the following can be known. As described above, when the characteristic frequency of the electrode polarization relaxation is sufficiently smaller than the frequency at which the cell to be measured causes the dielectric relaxation, it is possible to accurately measure the dielectric spectrum of a cell in the frequency range in which the cell causes the dielectric relaxation.

Here, when the cell to be measured is a corpuscle, the lowest frequency in the frequency range in which the corpuscle causes the dielectric relaxation is about 100 kHz as described above. The frequency band of the electrode polarization relaxation reaches a range obtained by increasing or decreasing the number of digits of the characteristic frequency by two digits. Accordingly, when the characteristic frequency $f_{EP}$ [Hz] of the electrode polarization relaxation in Expression 1 satisfies the following expression so as to clearly separate the frequency bands in which the corpuscle causes the dielectric relaxation and the electrode polarization relaxation, it is possible to accurately measure the dielectric spectrum in the frequency range in which the corpuscle causes the dielectric relaxation.

$$f_{EP} = \frac{1}{2\pi} \frac{G_t}{C_S} \leq 100 \qquad (9)$$

When the thickness of the electrical double layer is represented by "$r_D$", the surface area (of which the unit is m$^2$) of the electrode 12A or 12B is represented by "S", the relative permittivity of the solvent of the corpuscle is represented by "$\varepsilon_r$", and the vacuum permittivity is represented by "$\varepsilon_v$", the capacitance $C_s$ of the electrical double layer in Expression 9 can be expressed by the following expression.

$$C_S = \varepsilon_r \varepsilon_v \frac{S}{r_D} \qquad (10)$$

By arranging Expressions 9 and 10, the surface area S of the electrode can be expressed by the following expression.

$$S \geq \frac{G_t r_D}{100 \cdot 2\pi(\varepsilon_r \varepsilon_v)} \qquad (11)$$

For example, when the thickness (the length of the constriction portion in the direction in which a cell passes) of a layer constituting the constricted space CS of the flow channel 11 satisfying the conditions of $G_a > G_{bl}$ and $C_a > C_{bh}$ is 20 μm, the diameter (the length in the direction perpendicular to the direction in which a cell passes) of the constriction portion of the layer is 20 μm, and the solvent is physiological saline, the conductivity $G_t$ of the entire flow channel is substantially 26 μS. In this case, when the solvent of the corpuscle is physiological saline of which the relative permittivity $\varepsilon_r$ is 78, the surface area S of the electrode 12A or 12B has only to be greater than $4.4 \times 10^{-8}$ m$^2$.

Here, the numerical calculation result when it is assumed that the electrical double layer can be expressed by only the capacitance using the physical property values of the red corpuscle is shown in FIG. 10. The graph shown in FIG. 10 shows the relation among the dielectric spectrum of the solvent containing a cell to be measured, the spectrum of the electrode polarization relaxation due to the electrical double layer of the electrodes, and the measured value in the flow channel device 10 while changing the surface area S of the electrodes 12A and 12B to be disposed in the flow channel 11.

FIG. 10(A) shows an example where the surface area of the electrodes 12 to be arranged in the flow channel 11 satisfying the conditions of $G_a > G_{bl}$ and $C_a > C_{bh}$ is set to the surface area S at which the characteristic frequency $f_{EP}$ of the electrode polarization relaxation is 100 Hz (that is, an example satisfying Expression 9). In this case, the frequency of the dielectric relaxation of the solution containing the corpuscle which is caused in the frequency band equal to or higher than 100 kHz is sufficiently apart from the frequency band (substantially equal to or lower than 10 kHz) at which the electrode polarization relaxation is caused and it can thus be seen that it is possible to accurately measure the dielectric spectrum of a corpuscle.

On the other hand, FIG. 10(B) shows an example where the surface area of the electrodes 12 to be arranged in the flow channel 11 satisfying the conditions of $G_a > G_{bl}$ and $C_a > C_{bh}$ is set to the surface area S at which the characteristic frequency $f_{EP}$ of the electrode polarization relaxation is 10 kHz (that is, an example not satisfying Expression 9). In this case, the frequency band in which the electrode polarization relaxation is caused exists on a high frequency side, overlaps with the frequency band in which the dielectric relaxation of the solution containing the corpuscle is caused, and it can thus be seen than it is difficult to measure only the dielectric spectrum of the corpuscle.

In this way, when the thickness and the diameter of the constricted space CS of the flow channel 11 satisfying the conditions of $G_a > G_{bl}$ and $C_a > C_{bh}$ are 20 μm, the solvent of the corpuscles to flow in the flow channel 11 is physiological saline, and the surface area S of the electrode 12A or 12B is equal to or greater than $4.4 \times 10^{-8}$ m$^2$, the characteristic frequency of the electrode polarization relaxation is sufficiently smaller than the frequency at which the dielectric relaxation of the solution containing the corpuscles is caused.

Expression 11 is established on the assumption that the electrode 12A or 12B is specular, but is defined as the surface area of the electrode 12A or 12B serving as the electrical double layer in practice. For example, by performing surface treatment so as to make the surface of the electrode uneven, it is possible to increase the surface area S of the electrode 12A or 12B serving as the electrical double layer. The surface area of the electrode serving as the electrical double layer substantially means an area (hereinafter, also referred to as a "liquid-contact area") of a portion of the electrode 12A or 12B coming in microscopic contact with the solution containing the cells to be measured.

That is, when it is assumed that the electrodes 12A and 12B are a very thin square prism, a surface area of which one side is 200 μm or more is obtained from the calculation of Expression 11. However, when the electrode surface is made to be uneven to increase the liquid-contact area by 100 times or more, the condition of Expression 11 can be satisfied even with an extreme case of a side of about 20 μm.

The method of increasing the surface area of the electrode is not limited to the uneven surface treatment, but methods of performing special coating processes such as gold black plating, platinum black plating, or palladium plating on the surface of an electrode can be employed.

Here, the numerical calculation result different from FIG. 10 is shown in FIG. 11. In this example, flow channels 11 in which the diameter of the constricted space CS in the flow channel 11 satisfying the conditions of $G_a > G_{bl}$ and $C_a > C_{bh}$ is set to 12, 16, and 20 μm are prepared and an alternating voltage of 100 kHz is applied to the electrodes 12A and 12B of the flow channels 11. In the graph shown in FIG. 11, the relation between the diameter of a cell supplied to the constricted space CS and the conductance and capacitance of the constricted space CS is shown.

In the graph, the horizontal axis represents the diameter of a cell (d, [μm]) and the vertical axis represents the conductance (left: ΔG [μS], the capacitance (right: ΔC [fF]) at the low-limit frequency marked by logarithmic scales, and the solid line in the graph represents the threshold value distinguishable from noise.

The diameter of a cell is a diameter of a sphere having a volume equivalent to the volume of the cell. The threshold value is a value equivalent to the threshold value which can be distinguished from noise by a highest-sensitivity impedance analyzer made by Agilent Technologies Inc.

It can be seen from FIG. 11 that both the conductance and the capacitance of the constricted space CS become greater than the threshold value distinguishable from noise by setting the diameter or the thickness of the constricted space CS to at least double the diameter of the cell.

Accordingly, when the cell to be measured is a corpuscle, it is preferable that both the diameter and the thickness of the constricted space CS are equal to or less than 50 μm from the viewpoint of an S/N ratio. When the cell to be measured is a corpuscle, it is ideal that a diameter of the constricted space CS of the constriction portion 11 is 20 μm and the thickness thereof is 50 μm. The surface area S of the electrode to be arranged in the constriction portion 11 satisfying Expression 11 is substantially $1 \times 10^{-8}$ $m^2$.

In Expression 11, the complex capacitance $C_S$ of the electrical double layer in Expression 9 is expressed using the parameters such as the surface area S of the electrode, the thickness $r_D$ of the electrical double layer, the relative permittivity $\varepsilon_r$ of the solvent, and the vacuum permittivity $\varepsilon_0$. These parameters are uniquely determined when the size of the constricted space CS or the solvent to flow in the flow channel 11 is determined.

That is, when the surface area S of the electrode 12A or 12B to be arranged in the flow channel 11 satisfying the conditions of $G_a > G_{bl}$ and $C_a > C_{bh}$ substantially satisfies Expression 9, it is possible to measure the dielectric spectrum of the corpuscle with satisfactory accuracy and to accurately calculate the dielectric parameters or the physical properties.

In Expression 9, "100" is the lowest frequency in the frequency band in which the corpuscle causes the dielectric relaxation. Therefore, when the cell to be measured is not a corpuscle, "100" in Expression 9 is changed depending on the lowest frequency value in the frequency band in which the cell causes the dielectric relaxation.

[2-4. Advantages and the Like]

According to the above-mentioned configuration, in the flow channel device 10 of the dielectric cytometry system 1, the constriction portion 11A including the constricted space CS is disposed between the inflow port IF and the outflow port OF of the flow channel 11 (see FIG. 5). The flow channel 11 is divided into the inflow channel portion 11B and the outflow channel portion 11C with the constriction portion 11A as a boundary. The electrode 12A is disposed in the inflow channel portion 11B and the electrode 12B is disposed in the outflow channel portion 11C (see FIG. 5).

In the flow channel device 10, the conductance ($G_{bl}$) of the constriction portion 11A at the low-limit frequency is smaller than the combined conductance ($G_a$) of the inflow channel portion 11B and the outflow channel portion 11C. The capacitance ($C_{bh}$) of the constriction portion 11A at the high-limit frequency is smaller than the combined capacitance ($C_a$) of the inflow channel portion 11B and the outflow channel portion 11C (see FIG. 8 and Expression 8).

Therefore, in the flow channel device 10, when an alternating voltage is applied to the electrodes 12A and 12B, the internal potentials of the inflow channel portion 11B and the outflow channel portion 11C are substantially kept constant and a relatively large potential difference and the concentration of an electric field are caused in the constriction portion 11A (see FIGS. 6 and 7).

That is, although the electrodes 12A and 12B in the flow channel device 10 are disposed apart from the constricted space CS, the same electrical state as if electrodes having the same area as the constricted space CS are disposed on the top surface (inflow side) and the bottom surface (outflow side) of the constricted space CS is implemented, whereby the same electric field as that state can be applied. As a result, the flow channel device 10 can measure the complex permittivity of a single cell while using the electrodes much larger than the cell.

This operational advantage is similarly obtained even when the arrangement positions of the electrodes 12A and 12B are changed or the alignment error occurs. Therefore, according to this flow channel device 10, it is possible to design a flow channel with a high degree of freedom and to obtain constant measurement reproducibility regardless of the deviation in electrical characteristics due to the manufacturing processes or the member itself. Since the degree of freedom in design is high, it is easy to optimize the flow channel structure in which problems such as the staying of bubbles easily occur.

The processing precision of the constricted space CS dominates the measuring accuracy. For example, when a polymer film formed of polyimide or the like is processed to form the flow channel 11 having the constricted space CS, the thickness of the constricted space CS can be accurately defined by the thickness of the film itself industrially standardized. On the other hand, the aperture size of the constricted space CS can be formed with satisfactory precision by the use of a lithography technique. Accordingly, when a sheet-like polymer film is used as a material of the flow channel 11, it is possible to strictly manage the constricted space CS of the flow channel device 10.

When the flow channel 11 is formed of a polymer film, the toughness is more excellent than that in the case of glass. Accordingly, the substantial durability in measuring the complex permittivity is improved, which is advantageous in view of practical use.

As described above, the electrode polarization occurs at the interfaces between the surfaces of the electrodes 12A and 12B and the liquid solvent and the pseudo relaxation (electrode polarization relaxation) is caused due to the capacitance of the electrical double layer by the electrode polarization.

When the measurement is performed on the opposite plates like NPL 1, it is necessary to set the same electrode gap or electrode area as the size of a single cell so as to measure the dielectric spectrum of individual cells. However, when the electrode gap or the electrode area is set to the same as the size of a single cell, it is not physically possible to distinguish the dielectric relaxation of a cell and the electrode polarization relaxation.

A blood count system is known as an existing system measuring the complex permittivity. The system performs the measurement on two points in a DC and a high frequency range (about 20 MHz) but does not perform the measurement on a mid-frequency range (about 100 kHz to 10 MHz).

In general, it is known that the complex permittivity (dielectric spectrum) of each frequency varies depending on the difference in shape of red corpuscles and the variation is prominent particularly in a mid-frequency range (for example, see Biophysical Journal 95 (2008), pp. 3043-3047). It is also known that the complex permittivity in the mid-frequency range prominently varies depending on the intra structure of a cell (for example, see Bioelectrochemistry and Bioenergetics 40 (1996), pp. 141-145).

Accordingly, in the blood count system, it is not possible to separate the cells by types or to detect and separate a heterogeneous type from homogeneous cells or to analyze the composition or state of a cell, using only information electrically obtained.

From this point of view, regarding the constricted space CS of the flow channel 11 satisfying the conditions of $G_a > G_{bl}$ and $C_a > C_{bh}$, the variations of the capacitance and the conductance of the entire flow channel device 10 are determined as the capacitance and the conductance of the constricted space CS. The liquid-contact areas of the electrodes 12A and 12B to be arranged in the inflow channel portion 11B and the outflow channel portion 11C divided with the constricted space CS of the flow channel 11 satisfying the conditions as a boundary satisfy Expression 9.

That is, the frequency (characteristic frequency $f_{EP}$) at which the electrical double layers formed in the interface between the electrodes 12A and 12B and the solution containing cells to be measured cause the dielectric relaxation is expressed as a value obtained by multiplying ½π by a ratio of the conductance between the electrodes at the low-limit frequency to the capacitance of the electrical double layers. The liquid-contact areas of the electrodes 12A and 12B are defined so that this value is smaller by two digits than the lowest frequency in the frequency range in which a cell to be measured causes the dielectric relaxation.

Therefore, according to the flow channel device 10, it is possible to clearly separate and measure the dielectric relaxation of a cell to be measured and the electrode polarization relaxation. As a result, it is possible to separate the cells by types or to detect and separate a heterogeneous type from homogeneous cells or to analyze the composition or state of a cell with high accuracy.

In this way, when the conditions of $G_a > G_{bl}$ and $C_a > C_{bh}$ and the condition of Expression 9 are satisfied, it is possible to concentrate the potential on the constriction portion 11A and to enhance the sensitivity by clearly separating the dielectric relaxation of a cell to be measured and the electrode polarization relaxation, whereby it is very advantageous in view of the measuring accuracy.

According to the above-mentioned configuration, by employing the flow channel device 10 in which the inflow channel portion 11B and the outflow channel portion 11C are connected with the constriction portion 11A having the constricted space CS through which a single cell to be measured passes, it is possible to implement a dielectric cytometry system 1 with improved measuring accuracy.

3. Other Embodiments

In the above-mentioned embodiment, the corpuscles have been used as the biological sample. However, the biological sample is not limited to the corpuscles. Polymers such as cells, chromosomes, DNA (deoxyribonucleic acid), cDNA (complementary DNA), RNA (ribonucleic acid), and PNA (peptide nucleic acid) other than the corpuscles can be used as the biological samples.

In the above-mentioned embodiment, the physiological saline has been used as the liquid containing the biological sample, but liquids other than the physiological saline may be properly used depending on the types of the biological sample, as long as they are a liquid solvent.

In the above-mentioned embodiment, the overall shape of the flow channel device 10 is a rectangular parallelepiped, but is not limited to this shape. Various shapes such as a spherical shape or a cylindrical shape can be used.

In the above-mentioned embodiment, the flow channel 11 is hollow, but is not limited to this configuration. For example, a flow channel not having a partial, such as a recessed portion having a concave shape, wall may be employed as the flow channel.

The above-mentioned embodiment has employed a flow channel structure in which the inflow channel portion 11B and the outflow channel portion 11C are arranged in parallel in the state where they deviate from each other in the direction perpendicular to the flow direction fd and the constriction portion 11A is disposed at the ends of the inflow channel portion 11B and the outflow channel portion 11C in the direction perpendicular to the flow direction fd. However, the flow channel structure is not limited to the embodiment.

For example, a flow channel device having a flow channel structure shown in FIG. 12 in which the elements corresponding to those in FIG. 5 are referenced by the same reference signs can be employed. In this flow channel device, the inflow channel portion 11B and the outflow channel portion 11C are arranged in parallel in the same plane and the constriction portion 11A is disposed at the ends of the inflow channel portion 11B and the outflow channel portion 11C in parallel to the flow direction fd. The flow channel device having such a flow channel structure can vary in thickness, but the flow channel device 10 having the flow channel structure according to the above-mentioned embodiment can have a small surface area.

For example, a flow channel device having a flow channel structure shown in FIG. 13 in which the elements corresponding to those in FIG. 12(B) are referenced by the same reference signs can be employed. In the flow channel device shown in FIG. 13, the inflow channel portion 11B and the outflow channel portion 11C connect cell-moving spaces SP, through which cells flow and electrode-arranged spaces SP, in which the electrodes 12 are arranged. That is, the channel (flow channel) enabling the liquid containing a biological sample to be measured to flow has only to include a cell-moving channel and it is not essential to dispose the electrodes 12 in the moving channel.

The shapes (structures or volumes) of the inflow channel portion 11B and the outflow channel portion 11C are not limited to the same shape (FIGS. 5, 12, and 13), but may be different from each other. When the shapes of the channel portions 11B and 11C are different from each other and at least the relation between the channel portion and the constriction portion 11A satisfies the above-mentioned conditions, the same advantages as described in the above-mentioned embodiment can be obtained. In addition, the above-mentioned conditions are $G_a > G_{bl}$ and $C_a > C_{bh}$.

The flow channels of the inflow channel portion 11B and the outflow channel portion 11C are formed in a linear shape, but may be formed in a curved shape or a circular shape.

The constriction portion 11A is not limited to the configuration in which it is disposed perpendicular (FIGS. 5 and 13(A)) or parallel (FIGS. 12 and 13(B)) to the flow direction fd, but may be inclined about the flow direction fd. The position of the constriction portion 11A may be properly changed. The constriction portion 11A is provided with the taper inclined toward the constricted space CS, but the taper may not be provided.

The constricted space CS of the constriction portion 11A is a space through which a single biological sample (a cell in the above-mentioned embodiment) to be measured can pass. However, as long as the constriction portion 11A includes the inlet and the outlet corresponding to the size of the single biological sample, the constricted space CS may not have such a size through which a single sample can pass. For example, the channel length or the channel diameter of the constricted space CS may be several times the size of the single biological sample to be measured. In this case, the complex permittivity of one or several biological samples can be measured, which is advantageous for measuring biological samples smaller than a cell.

The shape of the constricted space CS is cylindrical, that is, the spatial shape of the constricted space CS is cylindrical. However, the spatial shape is not limited to the cylindrical shape, but many various shapes such as a spherical shape, a trapezoidal shape, a spherical ellipse shape, and a trapezoidal cone shape may be employed.

In the above-mentioned embodiment, the electrodes 12A and 12B are disposed in the side walls of the inflow channel portion 11B and the outflow channel portion 11C. However, the positions of the electrodes 12A and 12B are not limited to the side walls of the channel portions 11B and 11C, but may be located inside the walls or the channel spaces. As shown in FIG. 13(B), channels branched from the cell-moving channel may be provided independently of the cell-moving channel and the electrodes may be disposed in the branched channels. The electrodes have only to be disposed in a flow channel portion into which a cell flows and a flow channel portion from which a cell flows with the constricted space CS as a boundary. In addition, various shapes may be used as the shapes of the electrodes.

In the above-mentioned embodiment, an alternating voltage is applied to the electrodes 12A and 12B while changing the alternating voltage at a high speed and at plural prescribed frequencies (a so-called frequency-domain method). However, the application method is not limited to the above-mentioned embodiment, but an alternating voltage in which plural frequency components coexist may be applied (a so-called frequency-overlapping method). In this case, even when the number of frequencies to be applied is great, the alternating voltage at the corresponding frequencies can be satisfactorily applied until a cell passes through the constricted space CS. A step-like voltage may be applied and its time response may be measured (a so-called time-domain method). However, in this case, the complex permittivity calculator 30 needs to perform a process of performing a Fourier transform using a current corresponding to the alternating voltage in which plural frequency components coexist as a function of time to detect the frequency dependency. The frequency-domain method and the time-domain method may be combined.

A wave obtained by most simply superposing sine waves having plural frequencies may be used as a wave in which plural frequency components coexist. When a singular point where the amplitude is close to zero is generated in the superposed wave, the sine waves may be superposed with the phases of the sine waves properly disagreed with each other. In addition, for example, differential Gaussian waves, surface transverse waves (STW), Rayleigh waves (Surface Acoustic Waves), BGS (Bleustein-Gulyaev-Shimizu) waves, Lamb waves, Surface Skimming Bulk waves, or SH (Shear Horizontal) waves can be used.

INDUSTRIAL APPLICABILITY

The invention is applicable to the field of bio-industry such as biological experiments, follow-up or diagnosis of patients, or creation of medicines.

REFERENCE SIGNS LIST

1: DIELECTRIC CYTOMETRY SYSTEM
2: FLOW FORMING SYSTEM UNIT
3: MEASUREMENT SYSTEM UNIT
4: SEPARATION SYSTEM UNIT
5: CONTROL SYSTEM UNIT
10: FLOW CHANNEL DEVICE
11: FLOW CHANNEL
11A: CONSTRICTION PORTION
11B: INFLOW CHANNEL PORTION
11C: OUTFLOW CHANNEL PORTION
20: MEASURING SECTION
21: ALTERNATING VOLTAGE SOURCE
22: AMPEREMETER
30: COMPLEX PERMITTIVITY CALCULATOR
40: BIOLOGICAL SAMPLE ANALYZER
CS: CONSTRICTED SPACE
fd: FLOW DIRECTION

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. A flow channel device having formed therein a flow channel through which a liquid containing a plurality of biological samples flows, the flow channel device comprising:
   an inflow port for the flow channel;
   an outflow port for the flow channel in direct fluid communication with the inflow port;
   a constriction portion provided within the flow channel between the inflow port and the outflow port of the flow channel, the constriction portion including an inlet and an outlet, the length of the constriction portion in the direction perpendicular to the direction in which a cell passes is no more than 50 micrometers;
   an inflow channel portion located within the flow channel between the inflow port and the inlet to the constriction portion;
   an outflow channel portion located within the flow channel between the outlet to the constriction portion and the outflow port;
   a first electrode disposed along a first wall inside the flow channel within the inflow channel portion with the first electrode disposed apart from the inlet of the constriction portion such that the inlet of the constriction portion is formed only by one or more wall of the inflow channel portion;
   a second electrode disposed along a second wall inside the flow channel within the outflow channel portion with the second electrode disposed apart from the outlet of the constriction portion such that the outlet of the constriction portion is formed only by one or more wall of the outflow channel portion;
   at least one of the first electrode and the second electrode has a surface area greater than $1 \times 10^{-8}$ m$^2$, wherein the constriction portion directly connects the inflow channel portion having the first electrode disposed therein with the outflow channel portion having the second electrode disposed therein, such that the constriction portion is a boundary of each of the inflow channel portion and the outflow channel portion, and such that liquid flow from the inflow port through the inflow channel portion to the constriction portion directly connecting the inflow channel portion to the outflow channel portion is in a same direction as liquid flow from the constriction portion through the outflow channel portion to the outflow port; and a controller including a non-transitory computer-readable medium storing instructions, the controller programmed to execute the instructions to cause (i) a conductance between the inlet and the outlet of the constriction portion at a low-limit frequency to be smaller than a combined conductance of the inflow channel portion and the outflow channel portion, and (ii) a capacitance between the inlet and the outlet of the constriction portion at a high-limit frequency to be smaller than a combined capacitance of the inflow channel portion and the outflow channel portion.

2. The flow channel device of claim 1, wherein a surface area of at least one of the first electrode and the second electrode coming in contact with a liquid solvent is equal to or greater than an area in which relaxation due to an electrical double layer formed in an interface between surfaces of the first electrode and the second electrode and the liquid solvent does not overlap with dielectric relaxation due to the biological samples.

3. The flow channel device of claim 1, wherein when a characteristic frequency indicating electrode polarization relaxation due to an electrical double layer formed in an interface between surfaces of the first electrode and the second electrode and a liquid solvent is expressed by a value obtained by multiplying $1/2\pi$ by a ratio of conductance between the first electrode and the second electrode at the low-limit frequency to the capacitance of the electrical double layer, the value is lower than a frequency obtained by reducing a number of digits of a lowest frequency in a frequency band indicating dielectric relaxation due to the biological samples by two digits.

4. The flow channel device of claim 1, wherein when a characteristic frequency indicating electrode polarization relaxation due to an electrical double layer formed in an interface between the electrode surfaces and a liquid solvent is expressed by a value obtained by multiplying $1/2\pi$ by a ratio of the conductance between the electrodes at the low-limit frequency to the capacitance of the electrical double layer and when the capacitance of the electrical double layer is expressed by a value obtained by multiplying the relative permittivity of the liquid solvent and the vacuum permittivity by a ratio of the area of an electrode portion coming in contact with the liquid solvent to the thickness of the electrical double layer, the electrode portion coming in contact with the liquid solvent has an area satisfying a conditional relation that the characteristic frequency is lower than the lowest frequency of the frequency band indicating the dielectric relaxation due to the biological samples.

5. The flow channel device of claim 1, wherein the constriction portion includes a space through which a single biological sample of the plurality of biological samples passes.

6. The flow channel device of claim 1, wherein the inflow port and the outflow port of the flow channel are detachably connected to a coupling end and the first and second electrodes are detachably connected to a connection end.

7. The flow channel device of claim 1, wherein a diameter of the constriction portion is less than or equal to 50 μm.

8. The flow channel device of claim 1, wherein the inflow channel portion and the outflow channel portion are disposed in parallel in a first direction and deviate from each other in a second direction perpendicular to the first direction, and the constriction portion connects a first end of the inflow channel portion to a second end of the outflow channel portion in the second direction.

9. The flow channel device of claim 1, wherein the inflow channel portion and the outflow channel portion are disposed in parallel within the flow channel.

10. The flow channel device of claim 1, wherein the inflow channel portion and the outflow channel portion have a substantially same shape.

11. The flow channel device of claim 1, wherein a diameter of the constriction portion is smaller than a diameter of each of the inflow channel portion and the outflow channel portion.

12. The flow channel device of claim 1, wherein the inflow channel portion and the outflow channel portion have a substantially same size.

13. The flow channel device of claim 1, wherein an electrode surface of at least one of the first electrode and the second electrode comprises an uneven surface treatment that increases a surface area of the at least one of the first electrode and the second electrode.

14. The flow channel device of claim 1, wherein at least one of the first electrode and the second electrode has a surface area greater than $4.4 \times 10^{-8}$ m$^2$.

15. The flow channel device of claim 1, which further comprises a connection member configured to be attached to and detached from a dielectric flow cytometry system.

16. The flow channel device of claim 1, wherein the constriction portion includes a taper incline between the inflow channel portion and the outflow channel portion.

17. The flow channel device of claim 1, wherein the constriction portion is formed of a same material that forms the inflow channel portion and the outflow channel portion, and wherein the first electrode is located within the inflow channel portion adjacent to the material of the inflow channel portion and the second electrode is located within the outflow channel portion adjacent to the material forming the outflow channel portion.

18. The flow channel device of claim 1, wherein the same direction is a horizontal direction.

19. The flow channel device of claim 1, wherein the liquid flow through the constriction portion is horizontal.

20. The flow channel device of claim 1, wherein the constriction portion includes at least one tapered crest directly connecting the inflow channel portion to the outflow channel portion.

21. The flow channel device of claim 20, wherein the constriction portion includes opposed tapered crests directly connecting the inflow channel portion to the outflow channel portion.

* * * * *